United States Patent [19]

Dodge et al.

[11] Patent Number: 4,650,772

[45] Date of Patent: Mar. 17, 1987

[54] MONOCLONAL ANTIBODY STABILIZATION

[75] Inventors: Robert H. Dodge, Libertyville; Randall J. Avers, Palatine, both of Ill.

[73] Assignee: Abbott Laboratories, North Chicago, Ill.

[21] Appl. No.: 639,156

[22] Filed: Aug. 9, 1984

[51] Int. Cl.[4] ................... G01N 33/577; G01N 33/53
[52] U.S. Cl. ................... 436/548; 436/547; 436/825; 436/826; 530/367; 530/387; 530/389
[58] Field of Search ............... 435/188; 436/513, 548, 436/547, 825, 826; 260/112 R, 121; 530/367, 387, 389

[56] References Cited

U.S. PATENT DOCUMENTS

| | | | |
|---|---|---|---|
| 4,218,335 | 8/1980 | Mochida et al. | 252/408 |
| 4,439,421 | 3/1984 | Hooper et al. | 424/85 |
| 4,444,880 | 4/1984 | Tom | 435/7 |

*Primary Examiner*—Sidney Marantz
*Assistant Examiner*—Jack Spiegel

[57] ABSTRACT

A solution containing from about 0.25% to about 5% hydrolyzed ovalbumin by weight provides surprising thermal stabilization of monoclonal antibodies.

6 Claims, No Drawings

MONOCLONAL ANTIBODY STABILIZATION

TECHNICAL FIELD

This invention relates to compositions for the thermal stabilization of monoclonal antibodies, and thermally stable monoclonal antibody compositions.

BACKGROUND ART

A number of research, diagnostic and analytical techniques involve the use of monoclonal antibodies. These are homogeneous antibody preparations derived from hybridoma cell cultures. Unfortunately, a number of monoclonal antibody preparations are thermally unstable. This is a distinct disadvantage, since transportation and storage impose considerable thermal stress upon the antibody preparation.

Because of this disadvantage, many current applications for antibodies use polyclonal antibodies, i.e., antibodies produced by cells containing a variety of cell lines, as are obtained from animals, which naturally and spontaneously produce antibodies in polyclonal form. However, while these polyclonal antibodies offer better thermal stability, they have the disadvantage of limited specificity and are cross-reactive to antigens related to their intended antigen. This limits the accuracy and reliability of tests in which the polyclonal antibodies are used. For example, a polyclonal antibody specific for the therapeutic agents theophylline or aminophylline can exhibit cross-reactivity to other common xanthines, such as caffeine and theobromine. A patient whose blood theophylline level is being followed by immunoassay must abstain from coffee, tea, colas, cocoa, and similar materials, or risk producing a false high result in the assay. An immunoassay using a stable and more specific monoclonal antibody could minimize this problem. Thus, an art-recognized need exists for a method of stabilizing monoclonal antibody preparations against thermal damage, and for thermally stable monoclonal antibody compositions.

DISCLOSURE OF THE INVENTION

It has now been discovered that hydrolyzed ovalbumin, at a concentration of from about 0.25% to about 5% by weight in solution can impart thermal stability to a monoclonal antibody composition, so that the antibody is still usable after storage at 45° C. for seven days. Accordingly, this invention provides a method for stabilizing a monoclonal antibody against thermal degradation, comprising incorporating the antibody in a solution containing from about 0.25% to about 5%, preferably about 1% hydrolized ovalbumin, by weight. The invention also provides a thermally stable monoclonal antibody composition, comprising from 0.5 nmol to 0.5 $\mu$mol monoclonal antibody per ml., from about 0.25% to about 5% hydrolyzed ovalbumin by weight, and the balance water.

Ovalbumin is well known. It is a simple, heat-coagulable, water-soluble protein obtained from eggs. The stabilizing effects of regular ovalbumin are discussed in the literature. For example, Derwent Abstract 14904 E/08, abstracting a Japanese Patent Application of Mitsubishi Chem. Ind. KK, describes an "immune reaction stabilizer" containing serum albumin, egg albumin, or protein derived from collagen fiber. However, it has been determined that ovalbumin per se is incapable of conferring thermal stability on a monoclonal antibody preparation. Only when the ovalbumin has been hydrolyzed is such stability imparted. Hydrolyzed ovalbumin is an article of commerce and can be obtained in quantity from, for example, Sigma Chemical Company. It has been determined that the stabilizing effect is strongest at a concentration of about 1% by weight, and is reduced both at lower and higher concentrations. However, the effect is present over the concentration range of from about 0.25% to about 5% by weight.

The effectiveness and utility of the methods and compositions of this invention are illustrated by the following nonlimiting examples. Although all of the examples used a theophylline antibody for the sake of convenience, it should be understood that other monoclonal antibodies can also be stabilized by the practice of this invention.

EXAMPLE 1

Two compositions were made containing a mouse monoclonal antibody to theophylline, prepared by classical methods. One contained the monoclonal antibody in 1% chicken egg albumin (unhydrolyzed) (Sigma, #A-5503, lot 23F-8175) in 0.9% saline with 0.1% $NaN_3$ preservative, and the other composition contained the monoclonal antibody and about 1% hydrolyzed chicken egg albumin in 0.9% saline with 0.1% $NaN_3$ preservative. The compositions were prepared by adding mouse ascites fluid containing 1 mg. theophylline antibody per ml. to the foregoing solutions at a dilution of 1:177.8. The compositions were tested by generating calibration curves against seven solutions containing known concentrations of theophylline ranging from 0 $\mu$g/ml. to 40 $\mu$g/ml. The calibrations were performed on Day 0 and after 4 and 7 days of storage at 45° C. Table 1 summarizes the results.

TABLE 1

| | 0 | 2.5 | 5.0 | 10.0 | 20.0 | 40.0 | SPAN |
|---|---|---|---|---|---|---|---|
| UNHYDROLYZED OVALBUMIN Theophylline, $\mu$g/ml | | | | | | | |
| Day | | | | | | | |
| 0 | 219.24 | 204.13 | 188.93 | 166.82 | 137.59 | 105.47 | 113.8 |
| 4 | 201.38 | 185.35 | 171.01 | 150.25 | 124.11 | 96.23 | 105.15 |
| 7 | 191.11 | 172.91 | 160.76 | 140.78 | 115.17 | 89.60 | 101.51 |
| $\Delta$ mp* | 28.16 | 31.22 | 28.17 | 26.04 | 22.42 | 15.87 | 12.29 |
| HYDROLYZED OVALBUMIN Theophylline, $\mu$g/ml. | | | | | | | |
| Day | | | | | | | |
| 0 | 215.42 | 198.85 | 184.66 | 162.51 | 132.23 | 100.05 | 115.37 |
| 4 | 207.58 | 190.69 | 177.17 | 155.02 | 128.85 | 98.46 | 109.12 |
| 7 | 206.02 | 187.63 | 172.89 | 151.34 | 123.46 | 95.22 | 110.80 |
| $\Delta$ mp* | 9.4 | 11.22 | 11.77 | 11.17 | 8.77 | 4.83 | 4.57 |

*results are in arbitrarily established millipolarization units. 33-1097j

The span of the test indicates the range of test response versus the range of sample concentrations. The greater the span, the more subtle the gradations in sample concentration the test can distinguish. In this test, a span of at least 100 millipolarization units is considered acceptable. The $\Delta$mp among the tests indicates the change in absolute sensitivity of the test over time. A $\Delta$mp of 10-12 or less over seven days of storage at 45° C. is considered acceptable. The solution containing hydrolyzed ovalbumin showed a greater span than the solution containing ordinary ovalbumin. More important, the solution containing hydrolyzed albumin showed a markedly smaller deterioration in span during storage at 45° C., as well as a smaller deterioration in absolute sensitivity (Δmp).

EXAMPLE 2

A composition containing theophylline antibody as in Example 1 was prepared using 0.01% bovine gamma globulin (BGG) in 0.1M phosphate buffer at pH 7.4 as the stabilizing agent (with 1% $NaN_3$ preservative). Tests against a blank (0 µg/ml) theophylline standard showed a deterioration in sensitivity of 11 millipolarization units after only one day at 45° C.

EXAMPLE 3

An antibody composition was prepared as in Example 2 but containing 1.01% BGG. Tests against a blank theophylline standard showed a deterioration in sensitivity of 15 millipolarization units after only one day at the lower temperature of 37° C.

EXAMPLE 4

An antibody composition was prepared by adding 0.5% hydrolyzed gelatin (protein) to the composition of Example 2. Tests against a blank theophylline standard showed a deterioration in sensitivity of 23.4 millipolarization units after only one day at 45° C.

EXAMPLE 5

Theophylline antibody compositions containing 1% hydrolyzed ovalbumin were prepared in 0.9% saline and in distilled water to examine the effects of electrolytes. The pH of the saline-containing composition was about 5.5. The compositions were tested against blank and positive (40 µg/ml) theophylline standards, both at day 0 and after 7 days at 45° C. Results are shown in Table 2.

TABLE 2

| Theophylline | Day 0 | Day 7 | Δmp |
|---|---|---|---|
| 0.9% Saline | | | |
| 0 µg/ml | 210.81 | 208.25 | 2.56 |
| 40 µg/ml | 100.34 | 97.88 | 2.46 |
| Span | 110.47 | 110.37 | 0.10 |
| Distilled Water | | | |
| 0 µg/ml | 210.48 | 206.54 | 3.94 |
| 40 µg/ml | 100.49 | 95.82 | 4.67 |
| Span | 109.99 | 110.72 | 0.73 |

The results (span and Δmp) are within acceptable limits with both compositions, indicating that the saline affects the stabilization performance only slightly.

EXAMPLE 6

Theophylline antibody compositions containing hydrolyzed ovalbumin in 0.9% saline were prepared as in the foregoing examples, but varying in ovalbumin concentration from 0.25% to 5%. These were tested against blank and positive standards as in Example 5, over periods of from three to seven days. For comparison, gelatin-containing antibody compositions were also prepared, varying in gelatin content from 1% to 5%. These were also tested against blank and positive theophylline standards over periods of from three to seven days. Results, shown in Table 3, confirm that hydrolyzed ovalbumin is markedly superior to other proteins, such as gelatin. The results also indicate that a 1% concentration of hydrolyzed ovalbumin is preferable to 0.25% and 5% concentrations.

TABLE 3

| Theophylline | Day 0 | Day 3 | | Δmp |
|---|---|---|---|---|
| 0.25 Hydrolyzed Ovalbumin | | | | |
| 0 µg/ml | 232 | 222 | | 10 |
| 40 µg/ml | 90 | 89 | | 1 |
| Span | 142 | 133 | | 9 |
| 0.5% Hydrolyzed Ovalbumin | | | | |
| 0 µg/ml | 232 | 224 | | 8 |
| 40 µg/ml | 95 | 91 | | 4 |
| Span | 137 | 133 | | 4 |
| Theophylline | Day 0 | Day 4 | Day 7 | Δmp |
| 1.0% Hydrolyzed Ovalbumin | | | | |
| 0 µg/ml | 216 | 214 | 214 | 2 |
| 40 µg/ml | 84 | 85 | 84 | 0 |
| Span | 132 | 129 | 130 | 2 |
| 3.0% Hydrolyzed Ovalbumin | | | | |
| 0 µg/ml | 212 | 209 | 207 | 5 |
| 40 µg/ml | 86 | 87 | 86 | 0 |
| Span | 126 | 122 | 121 | 5 |
| 5.0% Hydrolyzed Ovalbumin | | | | |
| 0 µg/ml | 206 | 203 | 194 | 12 |
| 40 µg/ml | 90 | 86 | 89 | 1 |
| Span | 116 | 117 | 105 | 11 |
| 1.0% Gelatin | | | | |
| 0 µg/ml | 221 | 200 | — | 21 |
| 40 µg/ml | 86 | 83 | — | 3 |
| Span | 135 | 117 | — | 18 |
| 3.0% Gelatin | | | | |
| 0 µg/ml | 216 | 205 | — | 11 |
| 40 µg/ml | 102 | 95 | — | 7 |
| Span | 114 | 110 | — | 4 |
| 5.0% Gelatin | | | | |
| 0 µg/ml | 209 | 200 | 192 | 17 |
| 40 µg/ml | 109 | 102 | 101 | 8 |
| Span | 100 | 98 | 91 | 9 |

What is claimed is:

1. A method for stabilizing a thermally unstable monoclonal antibody against thermal degradation, comprising incorporating the antibody in an aqueous solution containing from about 0.25% to about 5% hydrolyzed ovalbumin by weight, whereby said antibody is thermally stabilized.

2. A method according to claim 1 in which the aqueous solution contains about 1% hydrolyzed ovalbumin by weight.

3. A thermally stable monoclonal antibody composition comprising an aqueous solution containing from 0.5 nmol to 0.5 umol thermally unstable monoclonal antibody per ml., and from about 0.25% to about 5% hydrolyzed ovalbumin by weight.

4. A composition according to claim 3 which contains about 1% hydrolyzed ovalbumin by weight.

5. A composition according to claim 4 which further contains about 0.9% sodium chloride by weight.

6. A composition according to claim 5 which has a pH of about 5.5.

* * * * *